(12) United States Patent
Wang

(10) Patent No.: US 6,443,918 B1
(45) Date of Patent: Sep. 3, 2002

(54) ADJUSTABLE SPLINT

(76) Inventor: Tzu C. Wang, 11848 Taylorcrest, Houston, TX (US) 77024

( * ) Notice: Subject to any disclaimer, the term of this patent is extended or adjusted under 35 U.S.C. 154(b) by 0 days.

(21) Appl. No.: 09/587,713

(22) Filed: Jun. 5, 2000

Related U.S. Application Data

(63) Continuation-in-part of application No. 09/407,480, filed on Sep. 28, 1999.

(51) Int. Cl.[7] .................................................. A61F 5/00
(52) U.S. Cl. .............................. 602/5; 602/21; 602/16
(58) Field of Search ........................... 602/5, 20–21, 602/23, 16; 128/878–879, 882, 845–846

(56) References Cited

U.S. PATENT DOCUMENTS

| | | | | |
|---|---|---|---|---|
| 1,389,741 A | * | 9/1921 | Cotton | 602/22 |
| 1,643,850 A | * | 9/1927 | Jones | |
| 3,698,389 A | * | 10/1972 | Guedel | 128/77 |
| 4,019,504 A | * | 4/1977 | Sterling | 128/88 |
| 4,299,210 A | * | 11/1981 | Santy | 602/20 |
| 4,384,571 A | * | 5/1983 | Nuzzo | 602/21 |
| 4,463,752 A | * | 8/1984 | Liao | 128/882 |
| 4,618,147 A | * | 10/1986 | Hurd et al. | 273/54 |
| 4,666,158 A | * | 5/1987 | Moro | 273/54 |
| 5,044,360 A | * | 9/1991 | Janke | 602/27 |
| 5,116,296 A | * | 5/1992 | Watkins | 482/91 |
| 5,538,499 A | * | 7/1996 | Schwenn et al. | 602/20 |
| 5,651,376 A | * | 7/1997 | Thompson | 128/878 |
| 5,716,336 A | * | 2/1998 | Hines et al. | 602/27 |
| 5,860,943 A | * | 1/1999 | Bloedau et al. | 602/16 |
| 6,293,918 B1 | * | 9/2001 | Wang | 602/20 |

* cited by examiner

*Primary Examiner*—Denise M. Pothier
(74) *Attorney, Agent, or Firm*—Trop, Pruner & Hu, P.C.

(57) ABSTRACT

An adjustable splint provides for adjustment in one of a plurality of selectable positions. The splint comprises a first splint member for supporting a first portion of a limb of a patient and a second splint member for supporting a second portion of that limb, on opposite sides of a joint. A pivot connects the first and second members. A releasable clasp lies along the limb of the patient, arranged so that fastening the splint to the limb effectively locks the clasp in the selected position. In one arrangement, the clasp comprises a leaf spring attached to the first member. At a free end of the spring, a latch is provided which engages one of a plurality of notches in the second member. In alternative arrangements, a longitudinal slot may be provided in the second member to provide a larger number of positions.

10 Claims, 9 Drawing Sheets

ADJUSTABLE SPLINT

CROSS-REFERENCE TO RELATED APPLICATION

This application is a continuation-in-part of copending U.S. Ser. No. 09/407,480, filed Sep. 28, 1999, entitled "ADJUSTABLE SPLINT."

FIELD OF THE INVENTION

This invention relates generally to therapeutic braces and, more particularly, to an adjustable splint for therapeutic support of a limb of a patient at a joint.

BACKGROUND

Splints or braces are typically used to hold joints of a limb, such as wrist or elbow joints, in a neutral position to promote healing of bone or other tissue. The angle at which these splints hold the joint has generally not been adjustable. The degree of flexation or extension of the joint, however, may vary from patient to patient and may even vary in an individual patient depending on the progress of the patient's therapy. For example, after a stroke or after the onset of a muscle attacking disease, for example, nerve palsy, a patient's hand may become closed or clenched and the wrist may be involuntarily fixed in a palmarflexion position. To restore the use of the hand, the patient may undergo a therapy to open the clenched fist and to urge the wrist towards a more neutral position. This can be accommodated by a splint, which can be adjustable at the joint to assume different positions. Such an adjustable splint for a wrist brace has been proposed by Klotz in U.S. Pat. No. 5,358,471. The mechanism proposed by Klotz, however, involves installing either individual machine screws or bolts and wing nuts at medial and lateral sides of the splint. There remains a need for improvement of such a splint to provide an easier mechanism for selecting the angle of flexion of the splint.

SUMMARY

In general, according to one embodiment, a splint for a limb of a person includes a first splint member having a shape conforming to a first portion of the limb and a second splint member having a shape conforming to a second portion of the limb. The splint further includes an adjustment mechanism to vary the relative angular position of the first and second splint members, the adjustment mechanism including first and second engagement members cooperable with each other at plural positions.

Other embodiments and features will become apparent from the following description, from the drawings and from the claims.

DETAILED DESCRIPTION

Figure 1:
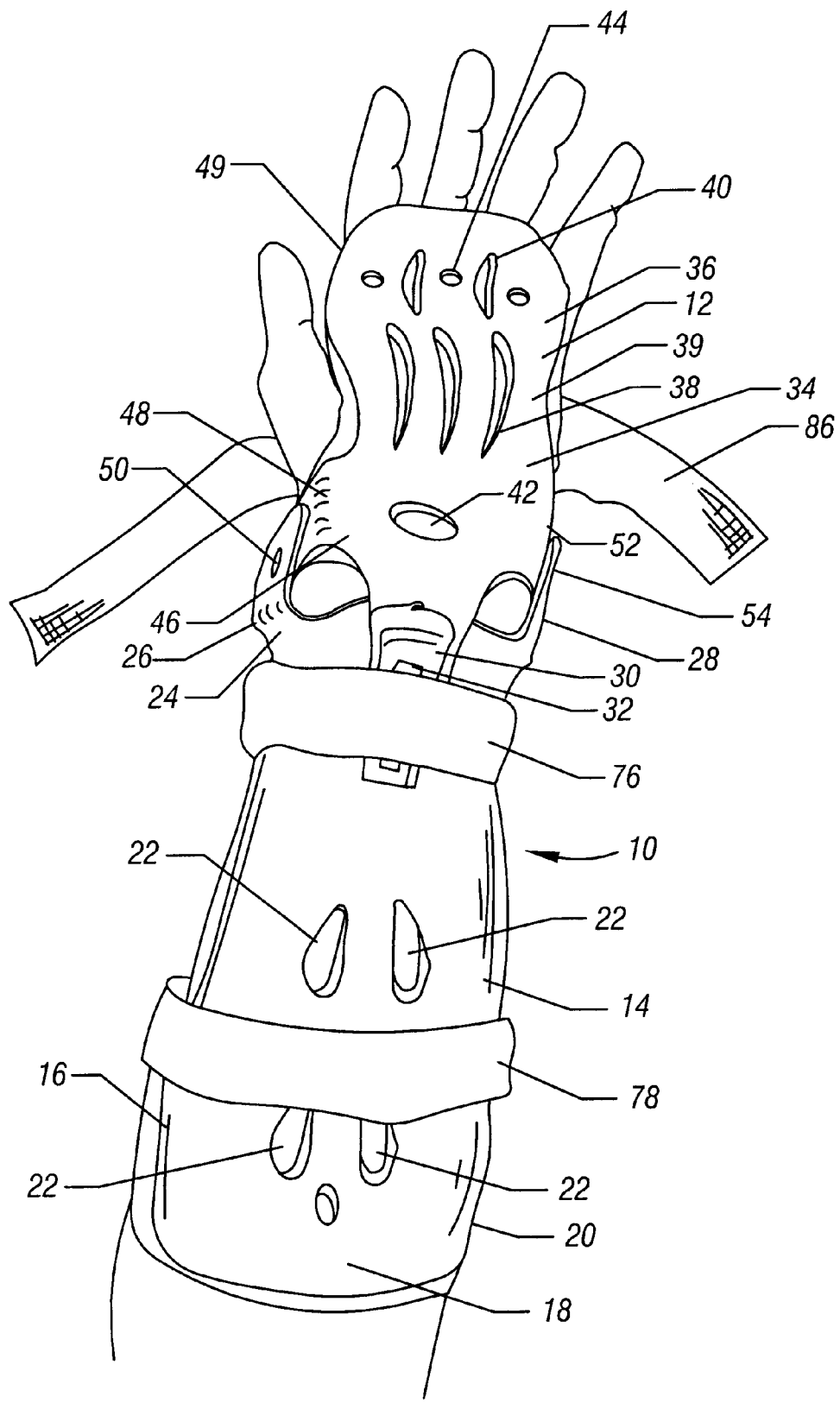
FIG. 1 is a perspective view of a splint according to an embodiment of the invention, in particular a wrist splint, illustrated supporting a forearm and hand of a patient.

Reference will now be made to the accompanying drawings in which like numerals are used to designate like parts throughout. FIG. 1 illustrates an inferior perspective view of a splint 10 according to an embodiment. In this embodiment, the splint comprises a wrist splint. However, splints according to other embodiments can be used for other joints of the body. The following description makes reference to specific structural arrangements of splints that are provided for purposes of illustration and better understanding of embodiments of the invention. However, it contemplated that other embodiments may have other arrangements.

The splint comprises a first substantially rigid member 12 or hand support and a second substantially rigid member 14 or forearm support. The first and second members 12, 14, are adapted to conform generally to their adjacent limb portion. The hand support 12 is, for example, adapted to conform generally to the palm of the hand. The forearm support 14 is adapted to conform generally to the shape of the forearm. The forearm support 14 comprises a lateral side 16, a bottom 18, and a medial side 20. Along the forearm support 14, ventilation holes 22 may be provided at selected locations. Such holes reduce the weight of the splint and provide for ventilation. The number and placement of such holes 22 is largely a matter of design discretion.

At a distal end 24 of the forearm support 14, a lateral pivot arm 26 extends distally from a lateral side 16 of the support. A medial pivot arm 28 similarly extends distally from the medial side 20 of the support. Also at the distal end 24, an exterior cavity 30 extends generally longitudinally at the distal end of the support 14. The function of this cavity will be explained in more detail hereafter.

Figure 2:
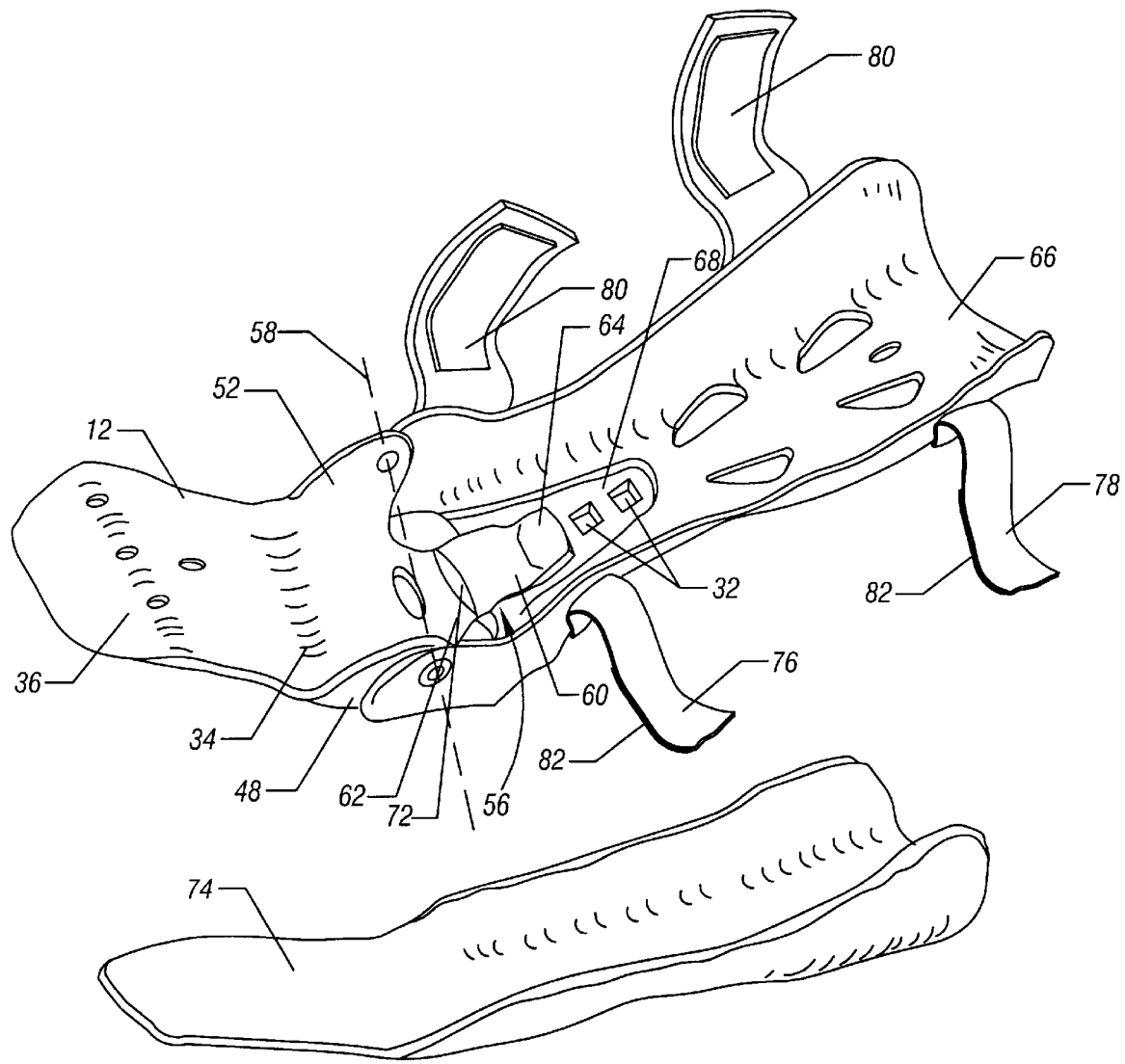
FIG. 2 is an exploded perspective view of the splint of FIG. 1.

The hand support 12 comprises a palm segment 34 and a finger segment 36. The palm segment 34 lies generally proximately and adjacent the distal end of the forearm segment 14. In one embodiment, the palm segment 34 has a slightly concave shape longitudinally on the side adjacent the patient's hand. The finger segment 36 extends distally and has a generally convex shape on the side adjacent the patient's hand, as best seen in FIG. 2. On an exposed side 39 of the hand segment 12, as seen in FIG. 1, the palm segment 34 is slightly convex and the finger segment 36 is concave. Additional rigidity for the hand segment 12 is provided by convex struts 38 on the palm segment and by concave struts 40 on the finger segment. Ventilation holes 44 may be provided in the finger segment, according to design discretion.

Figure 3:
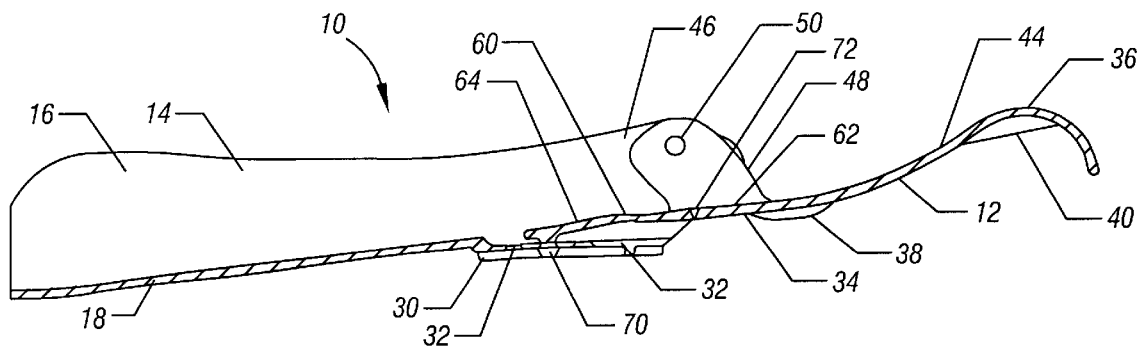
FIG. 3 is a plan view section of rigid members of the splint of FIGS. 1 and 2.

At a proximal end 46 of the hand support 12, a lateral pivot arm 48 engages the lateral pivot arm 26 of the forearm support. The two lateral pivot arms 26, 48 are connected by a swivel 50, which may be a rivet or other fastener. On the medial side, a medial pivot arm 54 on the hand support 12 engages the medial pivot arm 28 of the forearm support 14. A swivel 54 also connects the medial pivot arms. The swivels 50, 54 preferably have parallel axes and most preferably share a common axis configured to lie parallel to an axis of bending of the adjacent joint, in this instance, the wrist. The two swivels 50, 54 form a pivot that permits the joint, that is, the wrist, to be placed in a selected degree of flexion. The degree of flexion is selected using a self-locking clasp, which will now be described in connection with FIGS. 2, 3, and 4.

Figure 4:
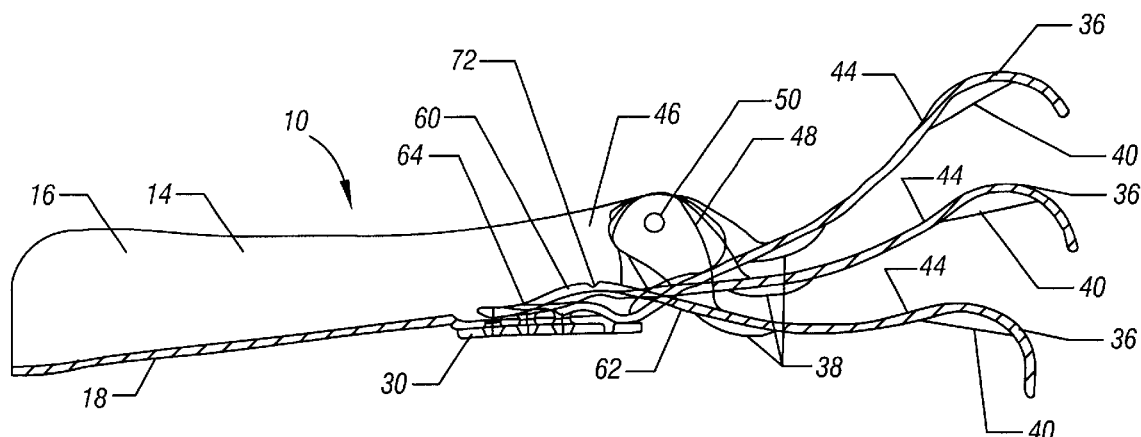
FIG. 4 is a plan view section similar to FIG. 3, illustrating multiple positions for a hand-supporting member of the splint.

The clasp 56 according to an embodiment provides an adjustment mechanism to adjust the relative mechanism to adjust the relative angular positions of the portions of the hand support 12 and the forearm support 14. The clasp 56 lies between the two swivels 50, 54 along a plane which generally bisects the splint 10 and is generally perpendicular to the axis 58 of the pivot for swivels 50, 54. The clasp 56 comprises a leaf spring 60 having a first end 62 attached to the first member, for example the hand support 12 and a second free end 64 which presses against the bottom 18 of the second member or forearm support 14 on an interior side 66. The leaf spring 60 rides in an interior cavity 68 and engages the notches 32 (formed in the forearm support 14) with a latch 70 seen in FIG. 3. Alternatively, the leaf spring 60 may be part of the forearm support 14 while the notches 32 are formed in the hand support 12. The latch 70 engages a selected one of the notches 32 to adjust the position of the first member or hand support 12 with respect to the second member or forearm support 14 as illustrated in FIG. 4. The number of notches is a matter of design discretion, with three notches illustrated in the example embodiment.

To control the spring action of the leaf spring 60, a relieved portion 72 may be provided at the first end of the leaf spring. In addition, an elliptical hole 42 in the palm segment serves both to provide ventilation and to increase the flexibility of the leaf spring 60. The elliptical shape of the hole, with a major axis perpendicular to the length of the leaf spring, effectively de-couples the first end 64 of the spring 60, allowing the spring to bend more freely. A foam pad 74 is generally provided to fit within the rigid members of the splint to provide additional comfort.

The action of the clasp 56 permits splints to be quickly oriented into a desired configuration or selected angle. When the limb of the patient is placed in the splint, the limb presses against the leaf spring 60 holding the latch 70 in a selected notch. Because the leaf spring 60 is substantially within the cavity of 68 the pressure of the splint against the forearm is generally uniform and the leaf spring does not abrade or irritate the arm of the patient. Straps 76, 78 may be provided to secure the splint 10 to the limb of the patient. Loop and eye fasteners 80, 82 may be provided to join the ends of the straps 76, 78. The straps may be attached to the splint, or may be separate portions. A distal strap 76 passes generally over the location of the clasp 56. This provides a secure pressure to hold the leaf spring 60 in engagement with the notches 32. The exterior cavity 30, described above, generally acts to prevent the strap 76 from coming in direct contact with the latch 70 so that the latch 70 will not be pressed out of anotch 32. Raised edges 84 around the exterior cavity 30 provide additional space between the strap 76 and the latch 70 to prevent contact with the latch 70 when, for example, a patient might rest their forearm on a table or other surface.

The patient's hand may similarly be secured to the hand support 12 using a strap or other fasteners such as a gauze bandage 86. In one embodiment, the splint 10 is bilaterally symmetrical, such that it can be used on right or left limbs, in particular at right or left wrists. The splint of my invention may be formed of injection-molded plastic or other suitable material. Where plastic is used, features such as the elliptical hole 42 and the relieved portion 70 become particularly important for controlling the flexibility of the leaf spring 60.

Figure 5:
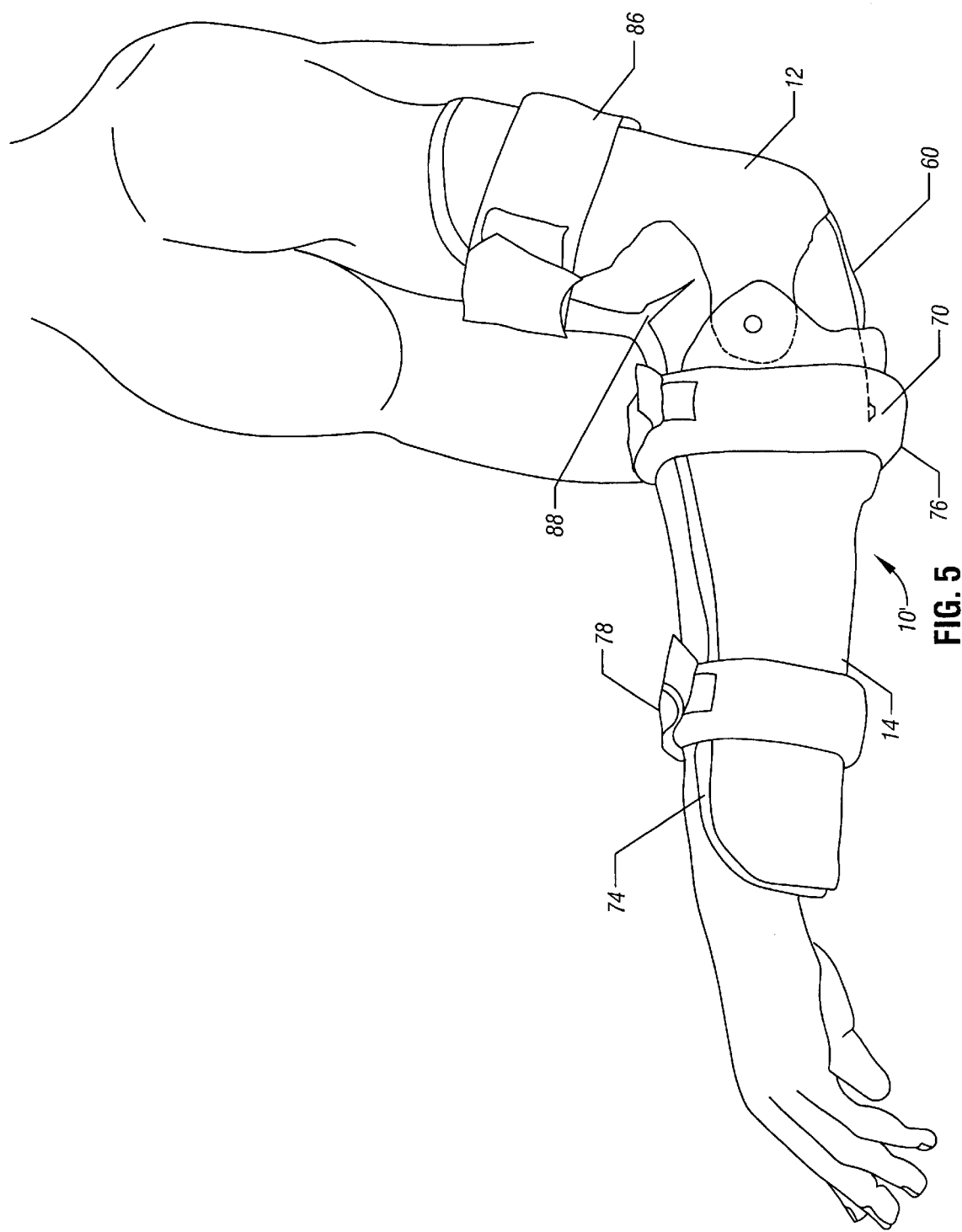
FIG. 5 is a plan view of an elbow splint, according to another embodiment of the invention, shown supporting the upper arm and forearm of a patient.

Splints according to further embodiments may be used for other joints of the body as, for example, the elbow as illustrated in FIG. 5. In the embodiment of FIG. 5 the splint 10 has the first rigid member 12 formed as a support for the upper arm and the second rigid member 14 formed as a support for the forearm. The spring 60 can be seen in phantom lines under the second rigid member 14, such that the latch 70 is under the strap 76. The pad 74 may have darts 88 cut or provided near the elbow joint to accommodate a relatively large degree of bending provided in this embodiment.

Figure 6:
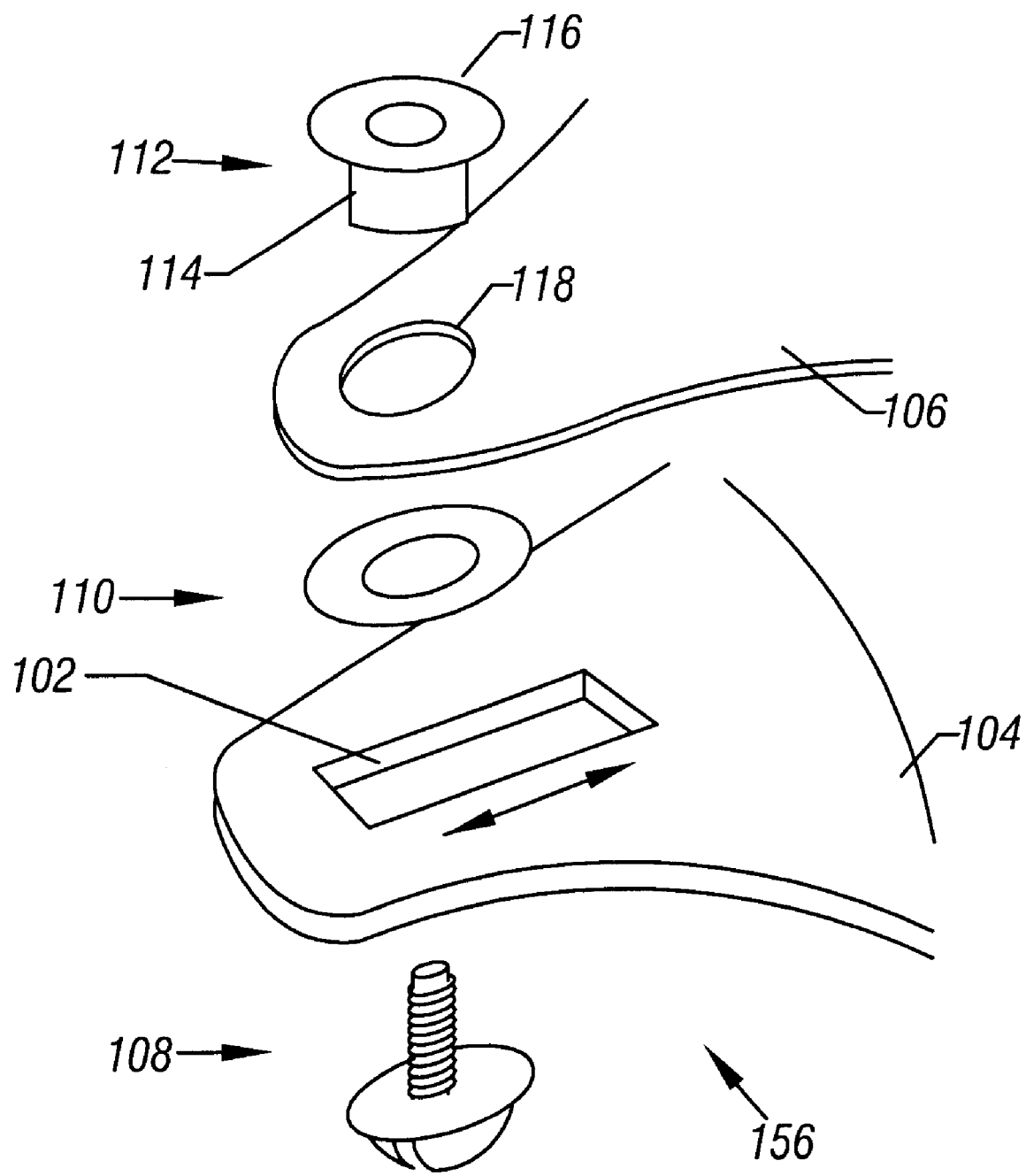
FIG. 6 is an exploded view of an adjustment mechanism of a splint in accordance with an alternative embodiment.
Figure 7A:
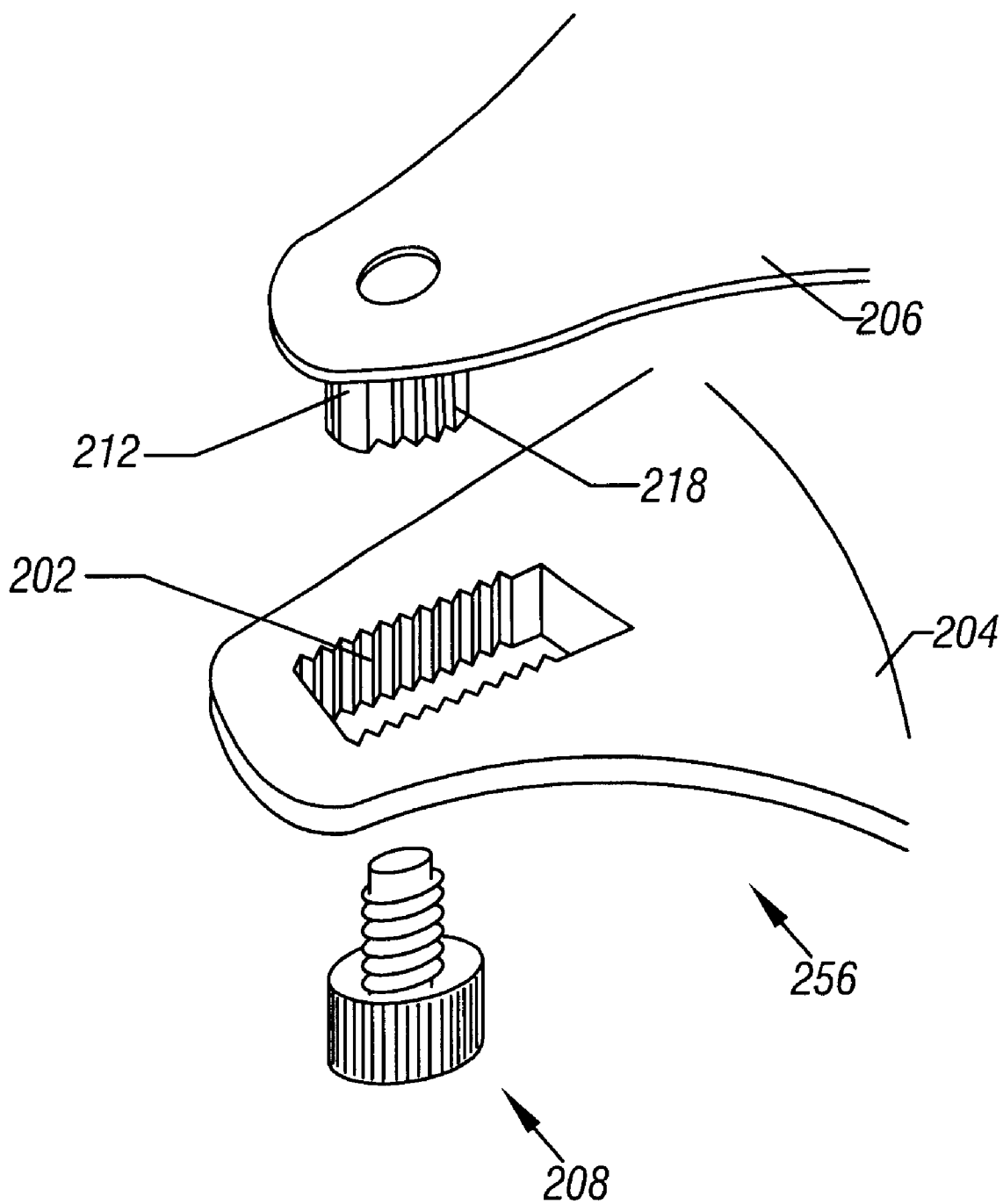
FIGS. 7A–7B are exploded views of an adjustment mechanism of a splint in accordance with yet a further embodiment.
Figure 7B:
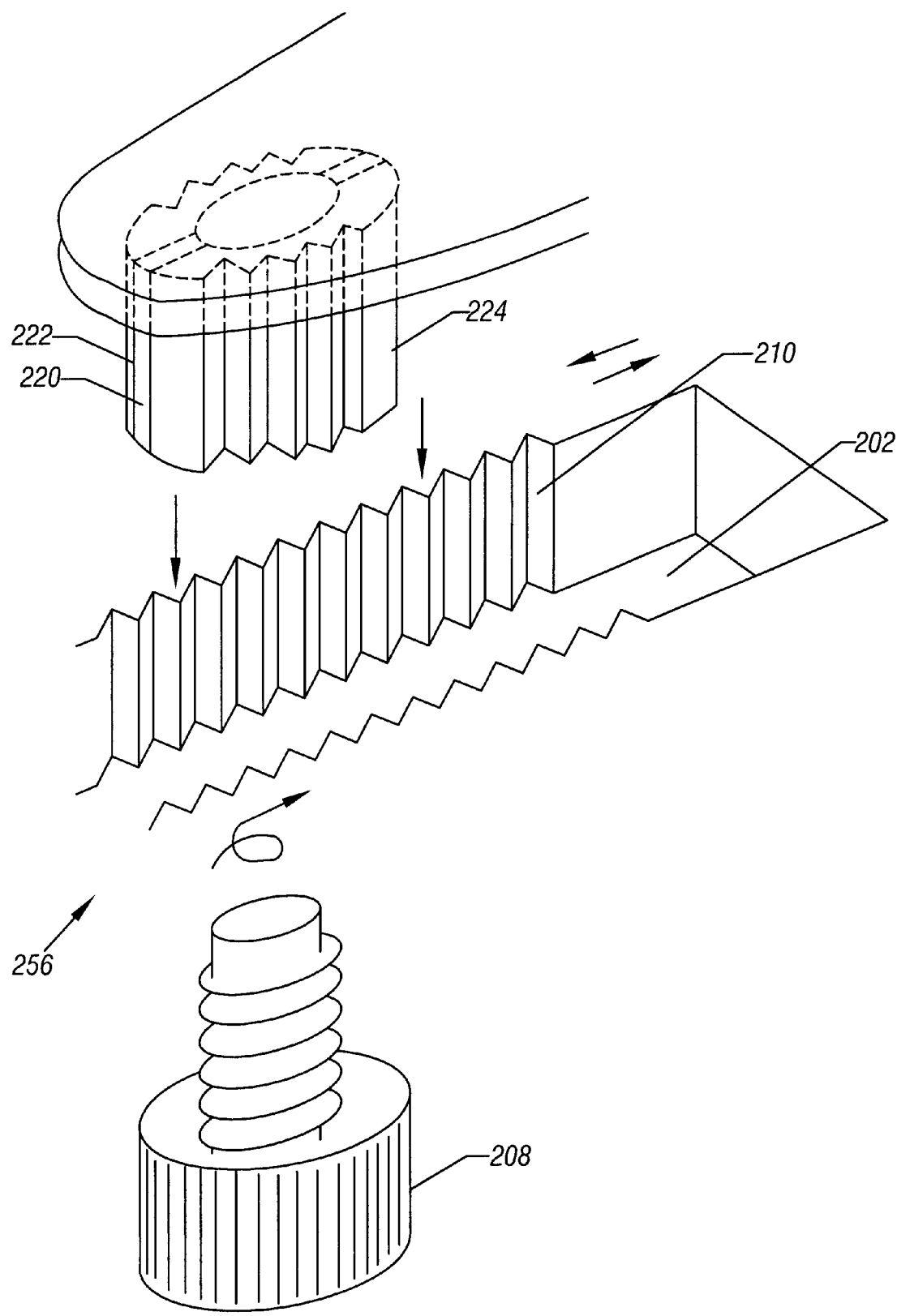

Referring to FIGS. 6 and 7A–7B, alternative embodiments of the adjustment mechanism between first and second splint members, similiar to that shown in FIG. 4 are illustrated. With the clasp 56 illustrated in FIGS. 2–4, adjustment of the relative angular positions of portions of the hand support 12 and the forearm support 14 are performed in discrete steps. In the illustrated embodiment of FIGS. 2–4, three discrete positions corresponding to the three notches 32 are provided. However, in the embodiment of FIG. 6, an adjustment mechanism 156 provides for continuously varying angular positions of the hand and forearm supports. In the embodiment of FIGS. 7A–7B, an adjustment mechanism 256 with a greater number of discrete positions (as compared to the clasp 56) is provided.

In FIG. 6, a longitudinal slot 102 is formed in a first split member 104, which may be one of a hand support, forearm support, or support for another limb. The slot 102 is generally along the axis of the first splint member 104. A bolt 108 may be engaged into the slot 102 from below. A washer 110 may be positioned between the upper surface of the first splint member 104 and the lower surface of a second splint member 106, which may form the support for another limb. A nut 112 having a generally cylindrical body 114 and an enlarged flange 116 is capable of threaded engagement with the bolt 108 when the cylindrical body 114 is placed into an opening 118 of the second splint member 106.

To adjust the relative angular positions of the first and second splint members 104 and 106, the bolt and nut assembly (including the bolt 108, washer 110, and nut 112) may be loosened and moved along the longitudinal slot 102 to a desired position. The bolt 108 is then tightened to the nut 112 to fix the relative position of the first and second splint members. In another embodiment, instead of the bolt and nut assembly shown in FIG. 6, another type of fastening assembly may be used that is moveable along the slot 102 when loosened or disengaged and fixed in position when tightened or engaged. Thus, generally, the adjustment mechanism includes a first engagement member arranged generally along an axis of the first splint member and a second engagement coupled to the second splint member cooperable with the first engagement member.

By providing continuously varying angular positions of the first and second splint members 104 and 106, greater flexibility is afforded to adjust the splint to the needs of the a patient.

In FIGS. 7A–7B, in accordance with another embodiment; the adjustment mechanism 256 provides a larger number of discrete positions to adjust relative positions of first and second splint members. FIG. 7B is an enlarged view of the adjustment mechanism of FIG. 7A. The adjustment mechanism 256 also includes a longitudinal slot 202. However, according to the FIGS. 7A–7B embodiment, the inner walls of the slot 202 are arranged with a teeth profile 210 that is engageable with an outer profile 218 of a nut 212 attached to the lower surface of the second splint member 206. The outer profile 218 has teeth that correspond to the teeth profile 210 of the inner walls of the slot 202.

A bolt 208 is insertable into the slot 202 for threaded engagement with the nut 212. The nut 212 has two segments 222 and 224 separated by a gap 220. A spring (not shown) in the nut 212 is adapted to push the segments 222 and 224 apart to push the outer profile 218 of the nut into engagement with the teeth profile 210 of the slot 202.

When making an adjustment of the relative positions of the splint members 204 and 206, the bolt 208 and nut 212 may be loosened and an operator may push the segments 222 and 224 of the nut 212 together so that the nut 212 is moveable longitudinally along the slot 202. Once a desired position is identified, the operator can release the nut 212 to allow the nut outer profile 218 to engage the slot teeth profile 210. The bolt 208 may then be turned to tighten the connection and fix the position of the splint members 204 and 206.

Figure 8:
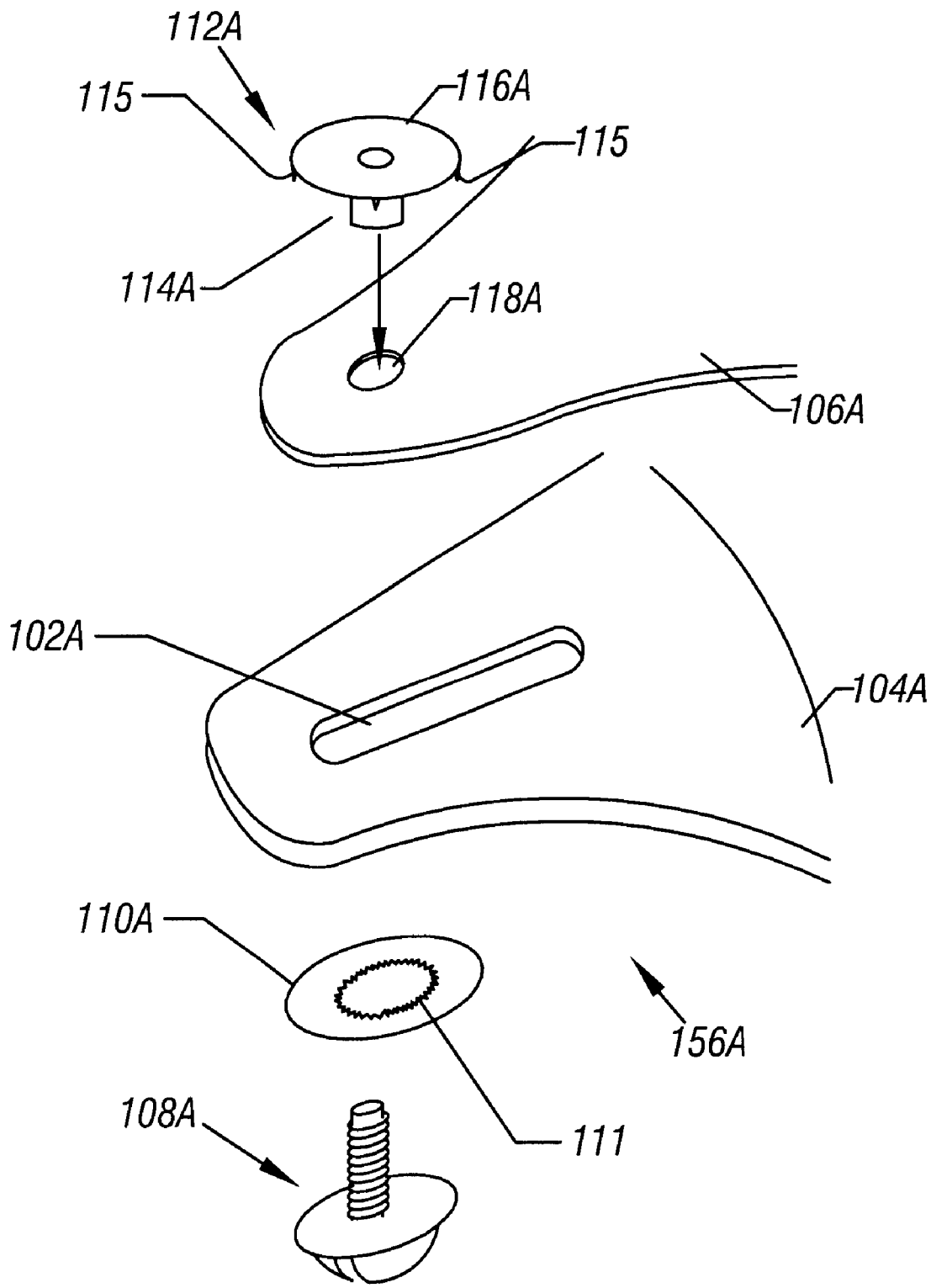
FIG. 8 is an exploded view of an adjustment mechanism of a splint in accordance with a further alternative embodiment.

Referring to FIG. 8, an adjustment mechanism 156A is a variation of the adjustment mechanism 156 shown in FIG. 6. As in the FIG. 6 embodiment, a longitudinal slot 102A is formed in first splint member 104A. The slot 102A runs generally along the axis of the first splint member 104A. A bolt 108A may be engaged into the slot 102A from below. A washer 104A may be positioned underneath the first splint member 104A, with the washer 110A including a teeth profile 111 along its inner circumference. The tooth profile 111 is provided to better secure the ring 110A to the bolt 108A to reduce likelihood of the bolt 108A rotating loose during use.

A second splint member 106A has an opening 118A through which a cylindrical body 114A of a nut 112A may be inserted for threaded connection to the bolt 108A. The nut 112A also has an enlarged flange portion 116A as well as sharp prongs 115 that depend from and are unitary with the enlarged flange portion 116A. The sharp prongs 115 are provided to engage the upper surface of the second splint member 106A to reduce the likelihood of rotation of the nut 116A once it is secured by the bolt 108A. The embodiment of FIG. 8 thus provides a more secure connection between the first and second splint members 104A and 106A as compared to the embodiment of FIG. 6.

Figure 9:
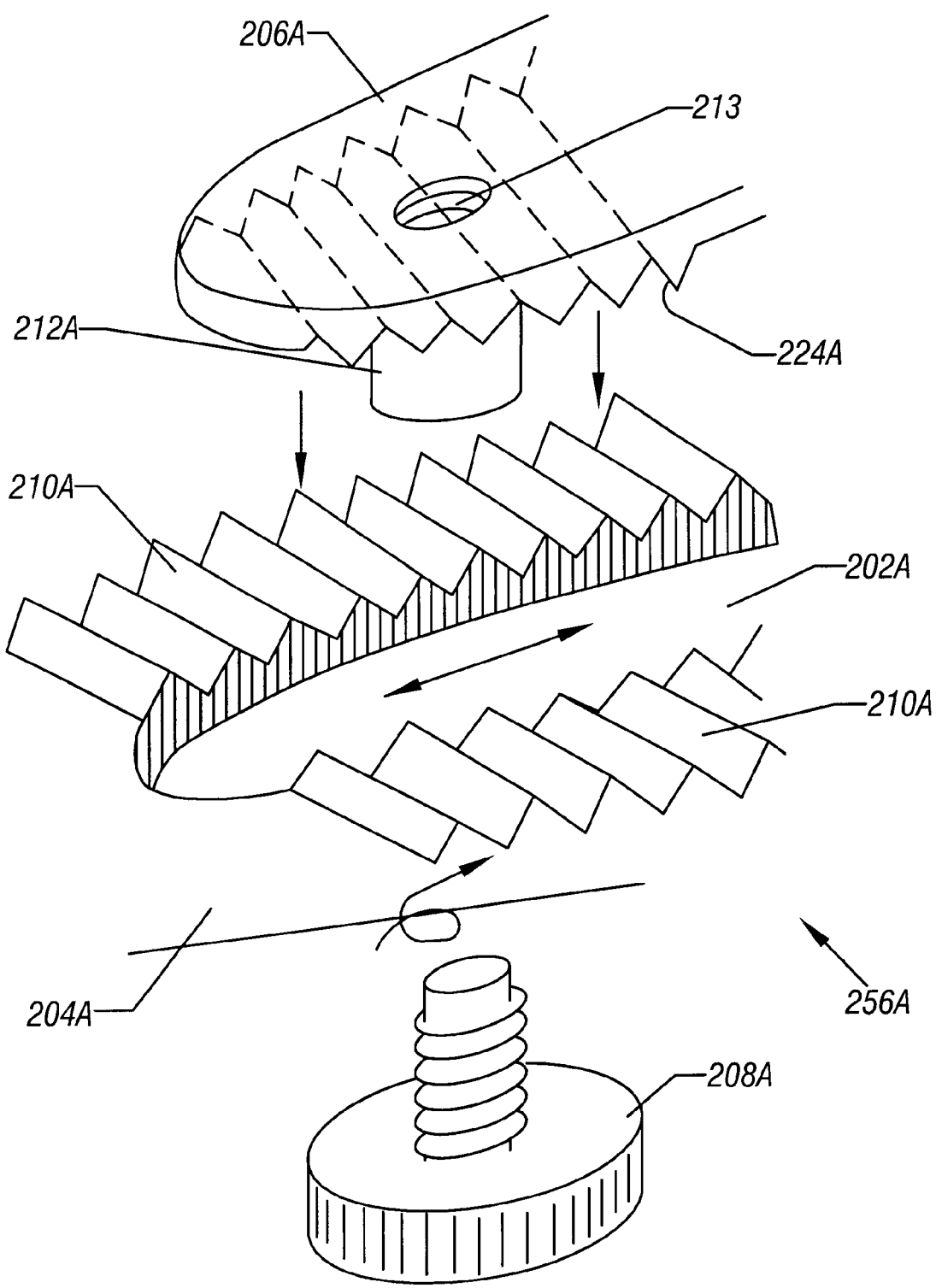
FIG. 9 is an exploded view of an adjustment mechanism of a splint in accordance with another embodiment.

Referring to FIG. 9, an adjustment mechanism 256A is illustrated that is a variation of the adjustment mechanism 256 of FIGS. 7A–7B. As in the embodiment of FIGS. 7A–7B, a first splint member 204A has a longitudinal slot 202A. One difference is that the slot 202A has a generally elliptical shape, while the slot 202 of FIGS. 7A–7B has a generally rectangular shape. Another difference is that teeth profiles 210A are provided on the upper surface of the first splint member 204A rather than the inner walls of the slot 202A. The teeth profiles 210A are adapted to engage corresponding teeth profiles 224A that depend from a second splint member 206A. A nut 212A is also attached to the lower surface of the second splint member 206A, with the nut 212A having a threaded inner bore 213 for engagement with the threaded profile of a bolt 208 A. As with the adjustment mechanism 256 of FIGS. 7A–7B, the adjustment mechanism 256A also provides a relatively large number of discrete positions to adjust relative positions of the first and second splint members 204A and 206A.

The foregoing examples of embodiments of the invention should be deemed exemplary only. Those skilled in the art will recognize that changes and modifications could be made in the design or construction without departing from the scope or teachings of my invention. It is intended, therefore, that the scope of the invention should be defined by the accompanying claims.

What is claimed is:

1. An arm and hand splint for a limb of a person, comprising:

a first splint member having a surface with a shape conforming to a palm of the person;

a second splint member having a surface with a shape conforming to a forearm of the person;

a pivot directly connecting the first and second splint members, the pivot having an axis generally parallel to each of the respective surfaces of the first and second splint members adapted to conform to the palm and forearm;

an angular adjustment mechanism to vary the relative angular position of the first and second splint members, the adjustment mechanism comprising a first engagement member coupled to the first splint member and a second engagement member arranged generally along a longitudinal axis of the second splint member, the first and second engagement members cooperable with each other at plural positions, wherein the second engagement member comprises a longitudinal slot along the longitudinal axis of the second splint member, the first engagement member moveable in the slot to a selected position; and wherein the first engagement member is cooperable with the slot to provide continuously varying angular positions of the first and second splint members.

2. The splint of claim 1, wherein the first engagement member comprises a nut and bolt assembly.

3. The splint of claim 1, wherein the pivot has plural swivels.

4. The splint of claim 1, wherein a cross section of the second splint member is generally U-shaped to conform to the forearm of the person.

5. An arm and hand splint for a limb of a person, comprising:

a first splint member having a shape conforming to a second portion of the limb;

an angular adjustment mechanism to vary the relative angular position of the first and second splint members, the adjustment mechanism comprising a first engagement member coupled to the first splint member and a second engagement member arranged generally along a longitudinal axis of the second splint member, the first and second engagement members cooperable with each other at plural positions, wherein the second engagement member comprises a longitudinal slot along the longitudinal axis of the second splint member, the first engagement member moveable in the slot to a selected position, wherein at least an inner side wall of the slot comprises a first profile and the first engagement member includes a mating profile to engage the first profile, wherein the shape of the first splint member conforms to a palm of the person, wherein the shape of the second splint member conforms to a forearm of the person, and wherein the splint further comprises a pivot connecting the first and second splint members.

6. The splint of claim 5, wherein a cross section of the second splint member is generally U-shaped to conform to the second limb portion.

7. A splint for a limb of a person, comprising;

a first splint member having a shape conforming to a first portion of the limb;

a second splint member having a shape conforming to a second portion of the limb;

an angular adjustment mechanism to vary the relative angular position of the first and second splint members, the adjustment mechanism having a first engagement member and a second engagement member, the first second engagement member cooperable with each other at plural positions, wherein the second engagement member comprises a longitudinal slot along a longitudinal axis of the second splint member, the first engagement member moveable in the slot to a selected position, the first engagement member comprising a nut and bolt, the nut having at least one prong extending from the nut and engaging a surface of the first splint member, wherein the nut comprises and enlarged flange portion, the at least one prong depending from and unitary with the enlarged flange portion.

8. The splint of claim 7, wherein the at least one prong comprises a sharp prong.

9. The splint of claim 7, further comprising:

a washer having an inner teeth profile adapted to engage the bolt.

10. A splint for a limb of a person, comprising;

a first splint member having a shape conforming to a first portion of the limb;

a second splint member having a shape conforming to a second portion of the limb;

an adjustment mechanism to vary the relative angular position of the first and second splint members, the adjustment mechanism having a first engagement member and a second engagement member, the first and second engagement members cooperable with each other at plural positions, wherein the second engagement member comprises a longitudinal slot along a longitudinal axis of the second splint member, the first engagement member moveable in the slot to a selected position, the first engagement member comprising a nut and bolt, the nut having at least one prong extending form the nut and engaging a surface of the first splint member, wherein the nut comprises an enlarged flange portion, the at least one prong depending from the enlarged flange portion, the splint further comprising at least another prong depending from the enlarged flange portion, wherein the shape of the first splint member conforms to a palm of the person, and wherein the shape of the second splint member conforms to a forearm of the person.

* * * * *

UNITED STATES PATENT AND TRADEMARK OFFICE
CERTIFICATE OF CORRECTION

PATENT NO. : 6,443,918 B1
DATED : September 3, 2002
INVENTOR(S) : Tzu C. Wang

It is certified that error appears in the above-identified patent and that said Letters Patent is hereby corrected as shown below:

Column 6,
Lines 41-42, " a first splint member having a shape conforming to a second portion of the limb", should be:

-- a first splint member having a shape conforming to a first portion of the limb;
   a second splint member having a shape conforming to a second portion of the limb; --

Column 7,
Line 22, "and" should be -- an --.

Signed and Sealed this

Twelfth Day of November, 2002

*Attest:*

JAMES E. ROGAN
*Attesting Officer*    *Director of the United States Patent and Trademark Office*